United States Patent
Johansson et al.

(10) Patent No.: US 9,827,050 B2
(45) Date of Patent: Nov. 28, 2017

(54) USER INTERFACE DEVICE FOR SURGICAL SIMULATION SYSTEM

(71) Applicant: SURGICAL SCIENCE SWEDEN AB, Göteborg (SE)

(72) Inventors: Christer Johansson, Olofstorp (SE); Anders Larsson, Mölndal (SE)

(73) Assignee: SURGICAL SCIENCE SWEDEN AB, Göteborg (SE)

( * ) Notice: Subject to any disclaimer, the term of this patent is extended or adjusted under 35 U.S.C. 154(b) by 357 days.

(21) Appl. No.: 14/647,477

(22) PCT Filed: Nov. 28, 2013

(86) PCT No.: PCT/EP2013/075000
§ 371 (c)(1),
(2) Date: May 27, 2015

(87) PCT Pub. No.: WO2014/083119
PCT Pub. Date: Jun. 5, 2014

(65) Prior Publication Data
US 2015/0289946 A1    Oct. 15, 2015

(30) Foreign Application Priority Data

Nov. 30, 2012  (EP) .................................. 12195067

(51) Int. Cl.
*A61B 19/00*      (2006.01)
*G09B 23/28*      (2006.01)
(Continued)

(52) U.S. Cl.
CPC .............. *A61B 19/50* (2013.01); *A61B 34/10* (2016.02); *A61B 34/25* (2016.02); *G09B 23/28* (2013.01);
(Continued)

(58) Field of Classification Search
CPC .............................. G09B 23/28; G09B 23/285
(Continued)

(56) References Cited

U.S. PATENT DOCUMENTS 5,623,582 A * 4/1997 Rosenberg ............. B25J 9/1689
                                                        345/161
5,731,804 A * 3/1998 Rosenberg ............. A63F 13/06
                                                        345/156
(Continued)

FOREIGN PATENT DOCUMENTS

CN        102262836 A      11/2011
DE        10304736 B3       9/2004
(Continued)

OTHER PUBLICATIONS

International Search Report for PCT/EP2013/075000, dated Feb. 21, 2014; ISA/EP.

*Primary Examiner* — Sam Yao
*Assistant Examiner* — William Ermlick
(74) *Attorney, Agent, or Firm* — Harness, Dickey & Pierce, P.L.C.

(57) ABSTRACT

A user interface device for a surgical simulation system, comprising a rigid shaft pivotably supported by a frame, and movable in the axial direction but fixed with respect to rotation around its longitudinal axis, and a handle having a sensor body rigidly attached to said rigid shaft, and a grip portion rotatable around said longitudinal axis relative said sensor body. The handle further comprises a rotator sleeve rotatable around said longitudinal axis relative said sensor body and said grip portion, a rotation sensor adapted to detect rotation of said rotator sleeve in relation to said sensor body, and a signal interface mounted on said sensor body and connected to receive a first detection signal from said rotation sensor. Through this design, all sensor elements and (Continued)

electronic circuitry can be provided in or adjacent to the sensor body, leading to an efficient design and manufacturing.

11 Claims, 4 Drawing Sheets

(51) Int. Cl.
| | | |
|---|---|---|
| *A61B 34/00* | (2016.01) | |
| *A61B 34/10* | (2016.01) | |
| *A61B 17/32* | (2006.01) | |
| *A61B 1/00* | (2006.01) | |
| *A61B 17/16* | (2006.01) | |
| *A61B 17/3207* | (2006.01) | |

(52) U.S. Cl.
CPC ........ *G09B 23/285* (2013.01); *A61B 1/00183* (2013.01); *A61B 17/1626* (2013.01); *A61B 17/1633* (2013.01); *A61B 17/32002* (2013.01); *A61B 17/320758* (2013.01)

(58) Field of Classification Search
USPC ........................................................ 434/262
See application file for complete search history.

(56) References Cited

U.S. PATENT DOCUMENTS

| | | | | |
|---|---|---|---|---|
| 5,762,255 A * | 6/1998 | Chrisman | ........ | A61B 17/07207 227/175.2 |
| 5,767,839 A * | 6/1998 | Rosenberg | ............. | A63F 13/06 345/156 |
| 5,805,140 A * | 9/1998 | Rosenberg | ............. | G01B 5/008 345/156 |
| 6,024,576 A * | 2/2000 | Bevirt | ...................... | G05G 9/04 345/158 |
| 6,057,828 A * | 5/2000 | Rosenberg | ............. | B25J 9/1692 345/156 |
| 6,323,837 B1 * | 11/2001 | Rosenberg | ............. | B25J 9/1689 345/156 |
| 6,377,011 B1 * | 4/2002 | Ben-Ur | ................... | G06F 3/016 318/566 |
| 6,437,771 B1 * | 8/2002 | Rosenberg | ............. | A63F 13/06 345/156 |
| 6,654,000 B2 * | 11/2003 | Rosenberg | ............. | B25J 9/1689 345/156 |
| 6,850,222 B1 * | 2/2005 | Rosenberg | ............. | G05G 9/047 345/156 |
| 6,902,405 B2 * | 6/2005 | Irion | ...................... | G05G 9/047 434/262 |
| 7,877,243 B2 * | 1/2011 | Olien | ...................... | G06F 3/016 345/156 |
| 8,403,674 B2 * | 3/2013 | Feygin | ................. | G09B 23/285 434/262 |
| 9,579,088 B2 * | 2/2017 | Farritor | ........... | A61B 17/00234 |
| 2001/0016804 A1 * | 8/2001 | Cunningham | ....... | G09B 23/285 703/7 |
| 2003/0068607 A1 * | 4/2003 | Gregorio | ............. | G09B 23/285 434/262 |
| 2003/0069719 A1 * | 4/2003 | Cunningham | ......... | G09B 23/28 703/7 |
| 2004/0024418 A1 * | 2/2004 | Irion | ...................... | G09B 23/28 606/205 |
| 2004/0045561 A1 * | 3/2004 | Alexander | ........... | G09B 23/285 128/897 |
| 2004/0101813 A1 * | 5/2004 | Irion | ...................... | G05G 9/047 434/262 |
| 2006/0084050 A1 * | 4/2006 | Haluck | ................... | G06F 3/011 434/365 |
| 2006/0099560 A1 * | 5/2006 | Gregorio | ............. | G09B 23/285 434/272 |
| 2007/0018958 A1 * | 1/2007 | Tavakoli | .................... | B25J 3/04 345/161 |
| 2007/0166682 A1 * | 7/2007 | Yarin | ................... | G09B 23/285 434/267 |
| 2009/0299711 A1 * | 12/2009 | Rosenberg | ............. | B25J 9/1689 703/6 |
| 2013/0196300 A1 * | 8/2013 | Huang | ................... | G09B 23/30 434/262 |
| 2013/0224710 A1 * | 8/2013 | Yang | ...................... | G09B 23/28 434/262 |
| 2013/0267975 A1 * | 10/2013 | Timm | ............ | A61B 17/320068 606/169 |
| 2013/0316318 A1 * | 11/2013 | Frank | ...................... | G09B 23/28 434/262 |
| 2013/0345701 A1 * | 12/2013 | Allen, IV | ............. | A61B 18/082 606/41 |
| 2014/0005682 A1 * | 1/2014 | Worrell | .......... | A61B 17/320092 606/130 |
| 2015/0272683 A1 * | 10/2015 | Yang | .......... | A61B 19/2203 606/130 |
| 2015/0289946 A1 * | 10/2015 | Johansson | ............ | G09B 23/285 434/262 |
| 2015/0325147 A1 * | 11/2015 | Johansson | ............ | G09B 23/285 434/262 |
| 2016/0117956 A1 * | 4/2016 | Larsson | ............... | G09B 23/285 434/262 |
| 2016/0249993 A1 * | 9/2016 | Farahmand | ............ | A61B 34/71 74/89.23 |
| 2016/0302653 A1 * | 10/2016 | Inoue | ...................... | G01C 3/08 |
| 2016/0335919 A1 * | 11/2016 | Larsson | ............... | G09B 23/285 |

FOREIGN PATENT DOCUMENTS

| | | | | |
|---|---|---|---|---|
| WO | WO-96-22591 A1 | 7/1996 | | |
| WO | WO 2007146894 A2 * | 12/2007 | ........... | A61B 17/062 |

* cited by examiner

USER INTERFACE DEVICE FOR SURGICAL SIMULATION SYSTEM

CROSS REFERENCE TO RELATED APPLICATIONS

This application is a 371 National Phase of PCT/EP2013/075000, filed on Nov. 28, 2013, which claims the benefit and priority of European Patent Application EP 12195067.9, filed on Nov. 30, 2012. The entire disclosures of each of the above applications are incorporated herein by reference.

FIELD

The present disclosure relates to a haptic user interface device for a surgical simulation system, and in particular a user interface device for simulating a laparoscopic procedure.

BACKGROUND

In recent years, systems for surgical simulations have become increasingly more used, in order to train physicians various surgical procedures without putting live patients at risk. In particular in the field of minimally-invasive surgery, such as laparoscopy, endoscopy, colonoscopy, etc., such simulation systems have gained significant acceptance. During minimal-invasive surgery the physician typically relies on an image on a screen rather than on an actual view of the patient, and with powerful image rendering available today, such an image can be simulated with a very high degree of realism.

In order to interact with the simulation software, the simulation system further requires an input device, i.e. hardware which the physician may operate and which simulates an actual surgical instrument. Such input devices should in physical appearance and function resemble an actual instrument. However, they must also provide sensor for detecting the current position of the simulated instrument, thereby enabling the simulation software to provide an appropriate image on the screen. In addition, such devices preferably include haptic feedback, i.e. provide feedback of forces that would be encountered during an actual procedure.

In the case of laparoscopy, an example of an input device is the Virtual Laparoscopic Interface (VLI) from Immersion Corp. This device includes a rigid shaft, corresponding to the instrument portion to be inserted into a patient, and a handle, with which the physician can move the instrument. In order to simulate the degrees of freedom of an actual instrument, which passes into a patient body through a small opening, the shaft is supported by a frame in a pivoting point with two degrees of freedom (rotation $\alpha$, $\beta$). In addition, the shaft can be translated in linear motion along its longitudinal axis, i.e. in and out of a simulated body, as well as rotated around this longitudinal axis. The handle further includes a grip portion, allowing the physician to operate a simulated surgical tool at the tip of the instrument. The input device contains sensors for all degrees of freedom including rotation of the shaft. Most sensors are provided in vicinity of the pivoting point, except the sensor of grip action, which is detected in the handle and provided through a separate signal interface on the handle. This signal interface is thus movable in relation to the frame, and connected to the frame with a cord. Just as in an actual instrument, the grip portion may further be rotated in relation to the rest of the handle, corresponding to an adjustment of the grip in relation to the working position. Such adjustment is not detected by sensors, and does not result in any force feedback.

Another example from Immersion Corp. is the Laparoscopic Surgical Workstation, (LSW). Just as in the VLI, the shaft will rotate when the handle is rotated, requiring detection of rotation in the pivoting point. However, in this case it is the grip portion that is fixedly attached to the shaft. In order to enable adjustment of the grip position, a rotatable sleeve is arranged in front of the grip portion, and rotation of this sleeve relative the handle is detected separately. Moving the grip (and the entire handle) in relation to the sleeve will thus rotate the shaft, but the relative rotation between grip and sleeve will be detected, so that the simulation software can interpret this as a grip adjustment rather than actual instrument rotation. Grip action is detected in the grip portion similar to the VLI. The LSW is a haptic device, i.e. it has actuators arranged to provide force feedback in all degrees of freedom. In terms of force feedback, rotating only the sleeve (which does not rotate the shaft) and rotating the entire handle (including the sleeve and the shaft) will result in the same force feedback.

Yet another example is the Laparoscopic Impulse Engine (LIE), also from Immersion Corp. In this example, the shaft has a rotationally fixed exterior tube which does not rotate. Instead, the handle rotates in relation to the tube, and this motion is transferred by an axle extending inside the tube to the distal end of the shaft, where it is detected by a rotation encoder. Detection of grip action is done similar to the LSW mentioned above, by a sensor provided on the upper side of the grip portion. The LIE therefore also requires two signal interfaces on the moving parts of the device, one in the distal end of the shaft, and one on the grip portion. Each of these interfaces needs to be connected to the frame with a cord.

A relevant patent documents in this context are U.S. Pat. No. 6,323,837 and U.S. Pat. No. 6,902,405.

Despite the many user interfaces that are already available, these solutions are mechanically and electrically complex, typically with electric circuitry distributed between several locations. Also, they fail to correctly mimic an actual surgical instrument, such as a laparoscope, due to multiple cables connected to the device, and in some cases cables connected to the grip portion.

SUMMARY

It is an object of the present disclosure to address the shortcomings of the prior art, and to provide an improved user interface device which is robust in function and cost effective to manufacture. Another object is to provide a user interface device which in use provides the user with an experience more closely resembling that of an actual surgical instrument.

According to the disclosure, these and other objects are achieved with a device comprising a rigid shaft having a primary extension along a longitudinal axis, the rigid shaft being pivotably supported by a frame, and movable in relation to the frame in the axial direction, but being fixed in relation to the frame with respect to rotation around the longitudinal axis, and a handle having a sensor body rigidly attached to the rigid shaft, and a grip portion rotatable around the longitudinal axis relative the sensor body, the grip portion being adapted to transform a gripping motion of a user into a linear displacement. The handle further comprises a rotator sleeve rotatable around the longitudinal axis relative the sensor body and the grip portion, a rotation sensor adapted to detect rotation of the rotator sleeve in relation to the sensor body, and a signal interface mounted on the sensor body and connected to receive a first detection signal from the rotation sensor.

Features of this design are 1) a shaft which is fixed with respect to rotation around its longitudinal axis, and 2) a handle which has a sensor body which is fixedly attached to the shaft, and a rotator sleeve which is rotatable relative to the sensor body. The combination of these features has not been previously disclosed, and provides several advantages compared to prior art user interface devices.

To begin with, all sensor elements and electronic circuitry can be provided in or adjacent to the sensor body, leading to an efficient design and manufacturing. Further, the signal interface, which also is provided on the sensor body, will be subject to translational movement, but not to any rotational movement around the longitudinal axis of the shaft. This reduces the amount of shear stress and wear on any cables or wiring connected to the signal interface, improving lifetime of the user interface device.

According to an embodiment, the handle further comprises a linear sensor mounted in the sensor body, and a displacement transfer arrangement for transferring any linear displacement generated in the grip portion to the linear sensor, wherein the signal interface is connected to receive a second detection signal from the linear sensor.

According to this embodiment, also grip action can be detected in the sensor body, so that no sensor circuitry is required in the grip portion. The grip portion can thus be a purely mechanical device, facilitating manufacture of the handle.

Further, as only one single signal interface is required (from the sensor body), only one cable or wire is required. In particular, the grip portion is completely free from cables or wiring.

In embodiments, the user interface device is arranged to provide haptic feedback to a user. For this purpose, a plurality of actuators may be mounted on the frame to provide force feedback when the shaft and handle are rotated or translated relative the frame. Typically, force feedback is provided in at least one linear and two rotational degrees of freedom.

Further, an actuator arranged to provide force feedback around a first axis (B) can advantageously be mounted on a part of the frame that rotates with said handle around a second axis (A). This means that a force transfer means, such as a drive belt or wire, extending between the actuator and the first axis will run in a fixed path, i.e. will not be subject to torsion or twist. This arrangement of force feedback actuators on the frame of a user interface device for a surgical simulation is considered to be novel and inventive per se, also without limitation to the features of the first teaching of the present disclosure.

The rigid shaft may have a rack on one side, which rack engages a gear wheel on said frame, thereby transforming a linear motion of the shaft into a rotation of the gear wheel. This design can be an effective way to enable detection of the shaft position, as well as force feedback by an actuator connected to the gear wheel.

BRIEF DESCRIPTION OF THE DRAWINGS

The present disclosure will be described in more detail with reference to the appended drawings, showing current embodiments of the disclosure.

DETAILED DESCRIPTION OF EMBODIMENTS

Figure 1:
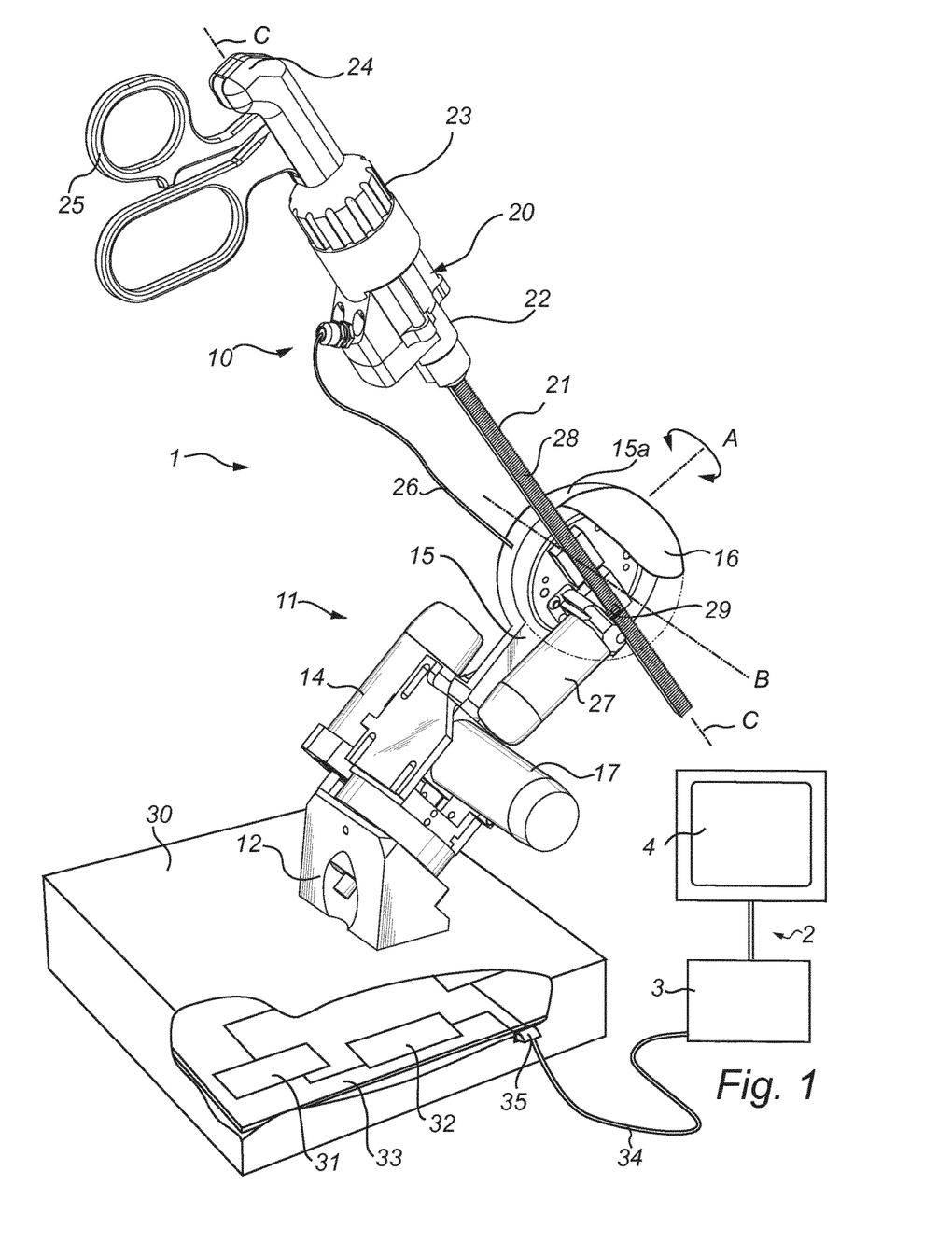
FIG. 1 is a schematic view of a surgical simulation system with a user interface device according to an embodiment of the disclosure.

FIG. 1 shows a user interface device 1 according to an embodiment of the present disclosure, schematically connected as part of a simulation system 2.

The simulation system 2 comprises a processing unit 3 running simulation software for simulating a surgical procedure, and a display 4 for displaying a visualization of the simulated procedure to a user. The interface device 1 is connected to the simulation system, and allows a user to provide input to the system 2, thereby interacting with the simulation visualized in the display device. The interface illustrated here is a haptic rig, i.e. it is adapted to provide a user with force feedback from the simulation in at least some of the degrees of freedom of the interface. It is noted that the disclosure is not limited to a haptic interface, but is also applicable to a non-haptic interface.

The user interface device 1, comprises a movable instrument 10 pivotably suspended by a frame 11. The frame 11 allows rotation of the instrument 10 around a first axis A and a second axis B, typically orthogonal to the first axis A.

Figure 2:
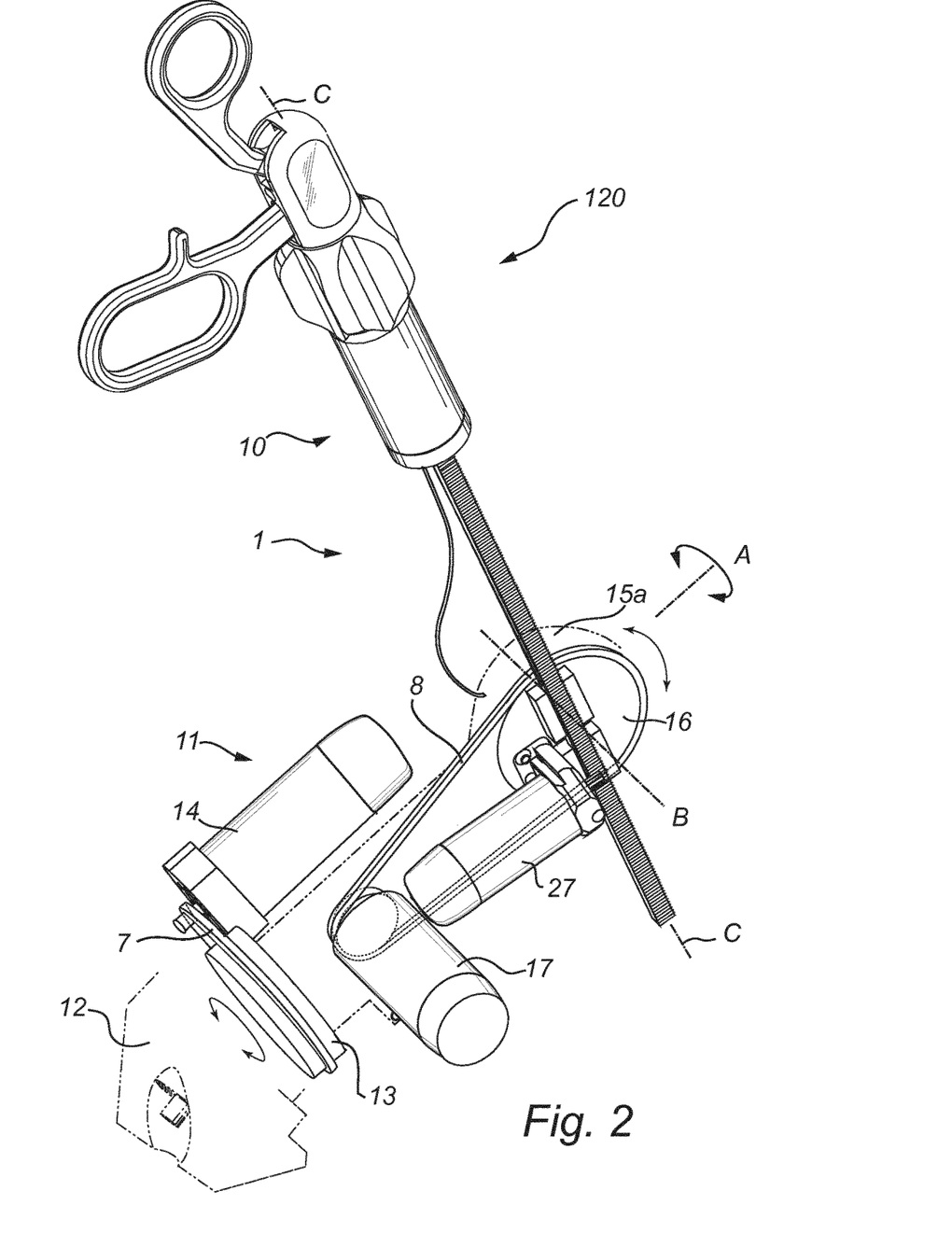
FIG. 2 is a schematic view of a surgical simulation system with a user interface device according to a further embodiment of the disclosure.

FIG. 2 very schematically shows some parts of the user interface device 1 in FIG. 1, in order to illustrate the various degrees of freedom in the frame 11. Note that the handle 120 in FIG. 2 is different from the handle 20 in FIG. 1.

In the illustrated embodiments, rotation around the first axis A is provided close to the stationary base 12 of the frame, by a disc 13 rotatably mounted to the base 12. A first actuator, such as a electric motor 14, is also mounted to the base 12, and arranged to transfer a torque to the disc 13. As illustrated schematically in FIG. 2, this can be accomplished by a driving belt 7 arranged around the disc 13 and the motor axle. By operation of the motor 14, force feedback can be provided in movement around the axis A. A rotation sensor (not shown) is provided to detect the position of the disc 13 in relation to the base 12. The sensor may advantageously be a rotational encoder integrated in the motor 14, and arranged to detect rotation of the motor axis.

Rotation around the second axis B is provided in a distal end 15a of the neck 15 of the frame 11. The neck 15 and its distal end 15a are fixedly mounted on the disc 13, and will thus rotate with the disc when the frame is rotated around the axis A. A suspension portion 16 is mounted on the distal end 15a so as to be rotatable around axis B. The suspension portion 16 is arranged to suspend the handle 10, and the details of this suspension will be discussed below. A second electric motor 17 is mounted on the neck 15, and is arranged to transfer a torque to the suspension portion 16. As illustrated schematically in FIG. 2, this can be accomplished by a driving belt 8 arranged around the portion 16 and the motor axle. By operation of the motor 17, force feedback can be provided in movement around the axis B. A rotation sensor (not shown) is provided to detect the position of the suspension portion 16 in relation to the distal end 15a of the neck 15. The sensor may advantageously be a rotational encoder integrated in the motor 17, and arranged to detect rotation of the motor axis.

Primarily with reference to FIG. 2, it is noted that the motor 17 is mounted on the neck 15, and thus will rotate together with the neck 15 and the suspension portion 16 around the axis A. The path of the drive belt 8 or drive wire loop extending between the axle of the motor 17 and the suspension portion 16 will thus be fixed in space, and will not be subject to any twist or torsion. This extends the life time of the belt 8 or wire.

It is noted that in the case of a non-haptic interface, in which case there are no actuators, sensors for detection of rotation around axis A and B is probably better provided directly on the axis A, B, e.g. on the disc 13 and the distal end 15*a*.

Turning now to the instrument 10, it comprises a handle 20 attached to the end of a rigid shaft 21. The handle 20 has a sensor body 22, fixedly connected to the shaft 21, and a rotator sleeve 23 and a grip portion 24 which are both rotatable around the longitudinal axis C of the shaft 21.

Just as in an actual instrument, rotation of the sleeve 23 represents rotation of the instrument. Any rotation of the rotator sleeve 23 in relation to the sensor body will thus be detected by a sensor in the sensor body 22. The grip 24 and rotator sleeve 23 are coupled by a certain friction so that they are normally rotated together. However, a user may overcome the friction, to rotate the sleeve 23 and the grip 24 in relation to each other. Rotation of the grip 24 while the sleeve 23 is held fix merely represents an adjustment of the grip in relation to the instrument, and will not influence the simulated procedure. Rotation of the sleeve 23 in relation to the sensor body while the grip 24 is held fix, will however represent rotation of the instrument and will accordingly be detected by the sensor body.

The grip portion 24 allows the user to perform a gripping action using a scissor-like grip 25, and this action will also be detected by a sensor in the sensor body 22. A signal line 26 connects the sensor body 22 with the frame 11, in the illustrated example with the distal end 15*a* of the neck 15. The signal line 26 enables communication of sensor signals from the sensor body 22. The signal line is flexible, so as to allow movement of the instrument 10 in relation to the frame 11.

In the illustrated embodiment, the interface device 1 is not adapted to provide any force feedback associated with rotation of the instrument around axis C. It is noted that there are typically very limited forces acting on an actual instrument in this degree of freedom when operated inside a body. However, if such feedback is nevertheless desired, it may be accomplished by coupling a force to the rotation of the sleeve 23 relative the sensor body. As a simple example, a passive variable brake can be provided to the sleeve 23. Such a brake would introduce a resistance to turning the sleeve, and this resistance can be variable depending on the simulation. Of course, also active force feedback can be envisaged with a suitable actuator, such as an electric motor. It is however important that such actuator, if mounted on the handle, is not too heavy or bulky, as it could otherwise impact negatively on the user experience.

The rigid shaft 21 is mounted to the suspension portion 16 of the frame 11 so as to be movable along the longitudinal axis C. A third electric motor 27 is mounted to the suspension portion 16 to transfer a force along the axis C to the shaft 21. By operation of the motor 27, force feedback can thus be provided along the axis C. A sensor (not shown) is provided in the suspension portion 16 to detect linear motion of the shaft in relation to the portion 16. In the illustrated example, the shaft 21 is provided on one side with a rack 28 which engages a gearwheel 29 on the end of a motor shaft. Any linear motion of the shaft 21 will thus effectively be converted into rotational motion, to which a torque can be applied by the motor 27. Detection of the linear motion is also facilitated, and the sensor may be a rotational encoder integrated in the motor 17, and arranged to detect rotation of the motor axis The base 12 of the frame 11 is mounted to a control unit 30, which includes drive circuitry 31 and communication interface 32, typically mounted on a printed circuit board 33. The control unit 30 can be incorporated in a working table (not shown). The interface 32 is connected to receive sensor signals from the various sensors in handle 10 and frame 11, and to communicate these signals to the simulation system 2. The interface 32 is further connected to receive force feedback signals from the simulation system 2, i.e. forces acting on the simulated instrument as a result of user actions. The drive circuitry 31 is connected to the interface 32, and arranged to drive the motors 14, 17 and 27 based on the force feedback signals from the simulation system. The interface 32 is here connected to the simulation system via a signal line 34 connecting a terminal 35 of the control unit 30 with the processing unit 3 of the simulation system. The connection may alternatively be wireless, e.g. Bluetooth or WiFi.

Figure 3:
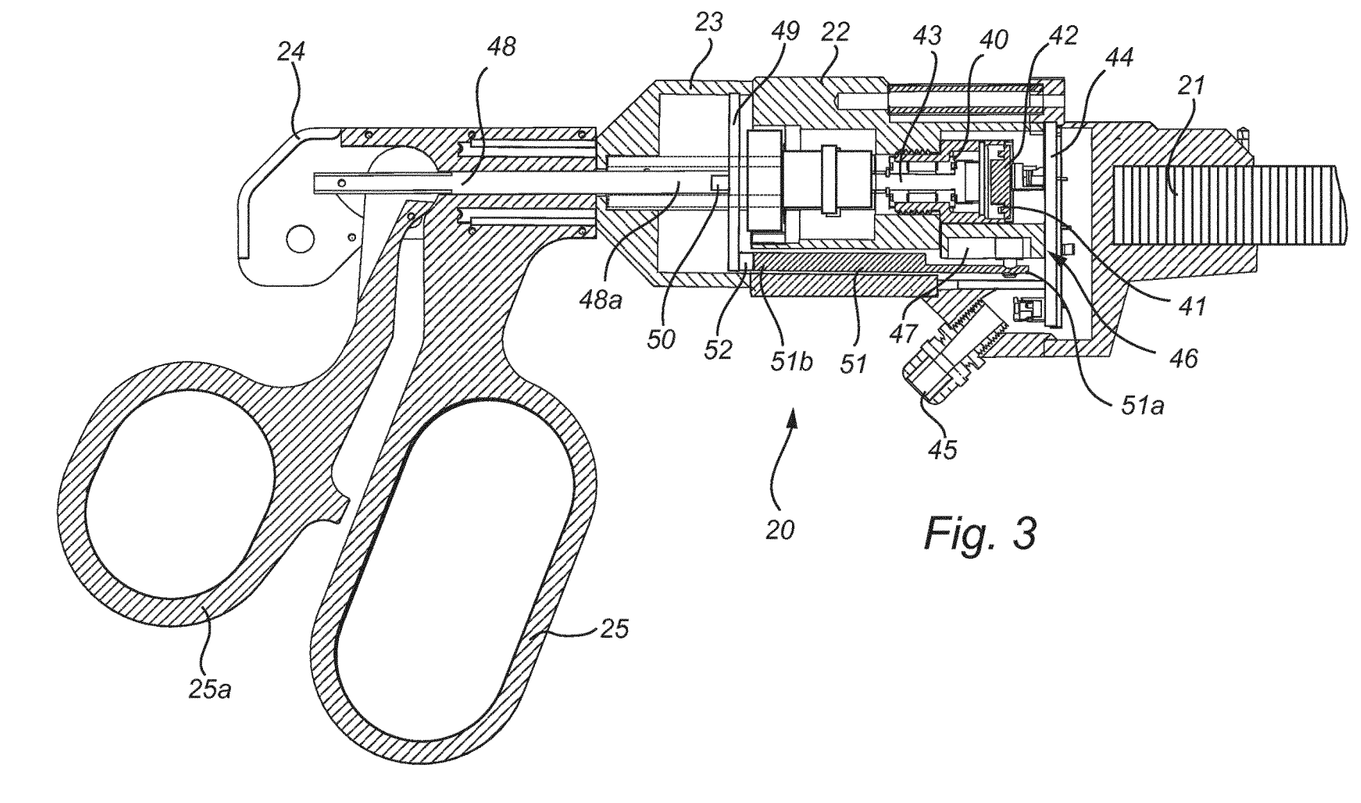
FIG. 3 is a side view of the handle in FIG. 1.
Figure 4:
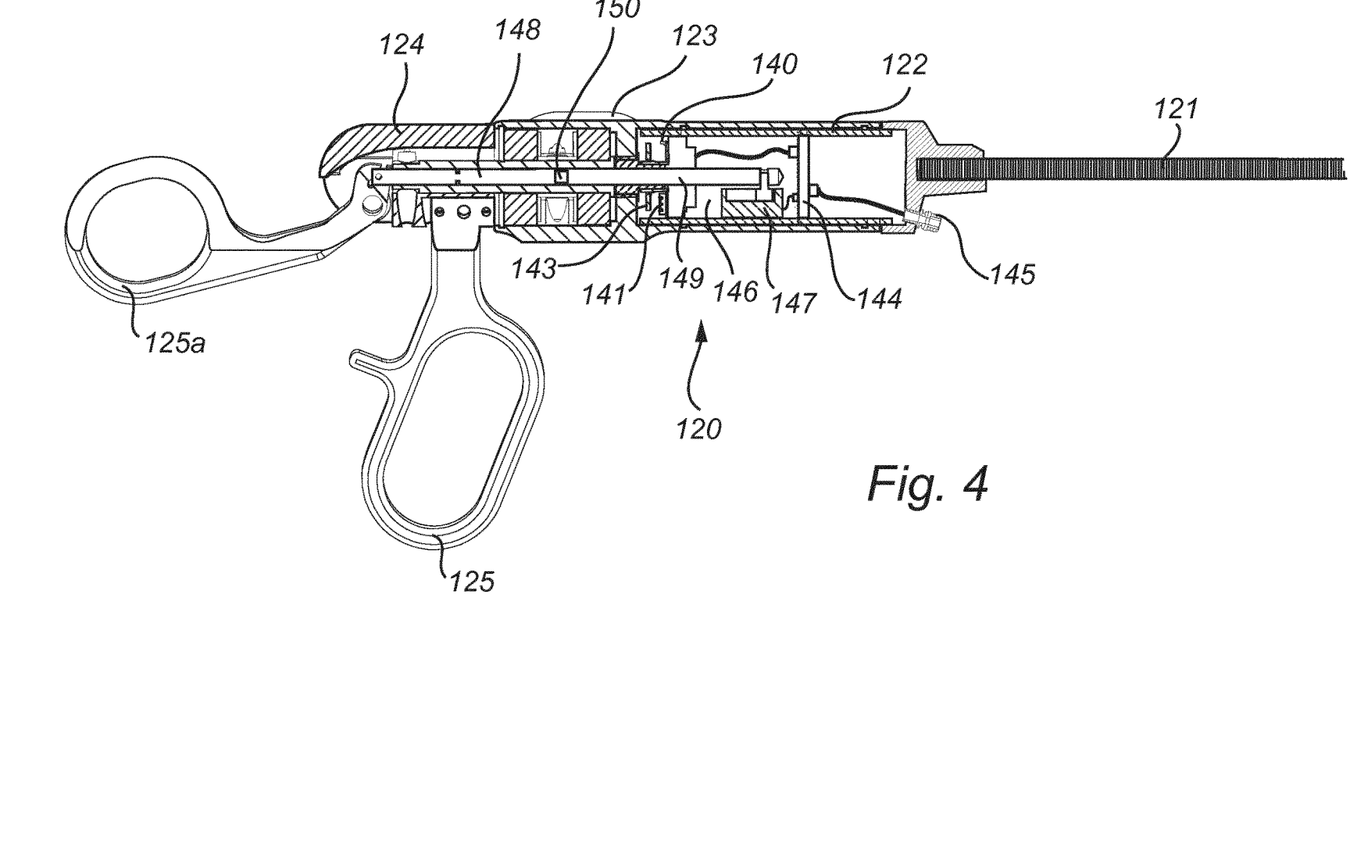
FIG. 4 is a side view of a handle in FIG. 2.

Details of the operation of the various parts of the handle, and in particular the sensor body, will now be discussed with reference to FIGS. 3 and 4 showing two different handles according to embodiments of the present disclosure.

FIG. 3 shows the handle in FIG. 1 in more detail. Reference numeral 40 denotes a rotation encoder, such as an optic or magnetic encoder mounted in the sensor body 22. The encoder 40 has a house 41, and a central pin 43 extending out of the house. Rotation of the pin 43 in relation to the house 41 can be detected, and results in a sensor signal indicative of the rotation. The encoder 40 is here in electric contact with circuitry on a printed circuit board 44, from which the sensor signal can be outputted via a terminal 45. The pin 43 of the encoder 40 is rotationally coupled to the rotator sleeve 23, which is rotatably connected to the sensor body 22. Rotation of the sleeve 23 will thus rotate the pin 43, and generate a sensor signal available at the terminal 45.

The grip portion 24 comprises a mechanical arrangement to generate a linear motion in response to action of the scissors-like grip 25. In the illustrated example, the rear part of the grip 25*a* is pivotable and connected to displace an elongate member 48 along the axis C. This linear motion is transferred by a motion transfer arrangement to a linear sensor 46 in the sensor body 22 in electric contact with circuitry on the circuit board 44. The linear sensor here includes a sliding potentiometer 47, the resistance of which is converted into a sensor signal indicative of a displacement of the potentiometer. Activation of the grip 25 will thus generate a sensor signal available at the terminal 45.

The motion transfer arrangement will be described in the following. The member 48 extends into the rotator sleeve 23, where it is mechanically connected to a disc 49 which is slidable inside the rotator sleeve 23 along the C-axis (see FIG. 1). The front end 48*a* of the member 48 is connected to the disc 49 in such a way that forces along the C-axis are transferred between the member 48 and the disc 49, while rotational forces around the C-axis are not transferred between the member 48 and the disc 49. As an example of such a coupling, the member 48 is illustrated as having a magnet 50 in its front end 48*a*, which magnet 50 is attracted to the central part of the disc 49. A second elongate member 51 has one end 51*a* mechanically connected to the slidable potentiometer 47, and another end 51*b* connected to the disc 49. Similar to the end 48*a* of the elongate member 48, the end 51*b* is connected to the disc 49 in such a way that forces along the C-axis are transferred between the member 51 and the disc 49, while other forces are not transferred between the member 48 and the disc 49. As an example of such a coupling, the member 51 is illustrated as having a magnet 52 in its end 51b, which magnet 52 is attracted to the peripheral part of the disc 49.

The motion transfer arrangement 48, 49, 50, 51, 52 operates in the following way. When the grip 25 is activated, the elongate member 48 is displaced along the C-axis. This displacement is transferred to the disc 49, so that the disc 49 is displaced along the C-axis inside the rotator sleeve 23. The displacement of the disc 49 is further transferred to the member 51, which displaces the slide potentiometer 47 of the sensor 46. When the linear displacement is towards the shaft 21, the member 48 will simply abut against and push the disc 49, which will abut against and push the member 51, so that motion will be transferred by direct contact. When the linear displacement is away from the shaft 21, the magnet 50 will attract the disc 49, which will attract the magnet 52, so that motion will be transferred by magnetic contact. When the grip portion 24 is rotated in relation to the sleeve 23, the elongate member 48 will also rotate, but this rotation will not cause any (substantial) forces on the disc 49. In the illustrated example, the magnet 50 will simply slip against the surface of the disc 49. In a similar way, when the rotator sleeve 23 is rotated in relation to the sensor body 22, the disc 49 will slide against the elongate member 51, without transferring any (substantial) force.

FIG. 4 shows a handle 120 according to a further embodiment of the disclosure. Similar to the handle 20 in FIG. 3, the handle 120 comprises a sensor body 122 fixedly connected to the shaft 121, and a rotator sleeve 123 and a grip portion 124, both rotatable around the longitudinal axis C of the shaft 121. Compared to the embodiment in FIG. 3, the rotator sleeve 123 is more elongated, and extends outside the sensor body 122 so as to cover most of the sensor body.

Also in this embodiment, the sensor body 122 houses a rotation encoder 140 to detect rotation of the rotator sleeve 123 relative the sensor body. The encoder is here an optical encoder, and the sensor optics of the encoder 140 includes a light transceiver 141 arranged on the sensor body side, and a reflector disc 143 arranged on the sleeve side. Rotation of the reflector disc 143 can be detected and results in a sensor signal indicative of the rotation. The encoder 140 is here in electric contact with circuitry on a printed circuit board 144, from which the sensor signal can be outputted via a terminal 145. The disc 143 is fixed to the sleeve 123, so that rotation of the sleeve 123 will generate a sensor signal which is available at the terminal 145.

The grip portion 124 is similar to the grip portion 24 in FIG. 3, and has a scissor-like grip 125 which can be operated by a user to generate a linear motion. Also here, the rear part of the grip 125a is pivotable and connected to displace an elongate member 148 along the axis C. This linear motion is transferred by a motion transfer arrangement to a linear sensor 146 in the sensor body 122 in electric contact with circuitry on the circuit board 144. Also in this case the linear sensor includes a sliding potentiometer 147, the resistance of which is converted into a sensor signal indicative of a displacement of the potentiometer. Activation of the grip 125 will thus generate a sensor signal available at the terminal 145.

The motion transfer arrangement in the embodiment in FIG. 4 is different from the arrangement in FIG. 3. In addition to the elongate member 148, the arrangement here comprises a second elongate member 149, aligned with the first elongate member 148 along the central axis C of the handle. The second elongate member 149 is coupled to the slide potentiometer 147, and extends through a hole in the center of optical encoder (i.e. the transceiver 141 and the reflector disc 143). The members 148 and 149 are mechanically connected such that forces along the C-axis are transferred between the members, while rotational torque is not transferred (to any significant degree). In the illustrated example, a magnet 150 is arranged on the end of member 148, and is attracted to member 149. The magnet 150 will connect the members 148, 149 in the axial direction, while it will slip against the member 149 when the members 148, 149 are rotated relative each other.

The person skilled in the art realizes that the present disclosure by no means is limited to the embodiments described above. On the contrary, many modifications and variations are possible within the scope of the appended claims. For example, other types of sensors and encoders may be used, for detection of rotation as well as translation. For example, hall effect sensors or piezoelectric sensors. Further, the torque transmission from motors 14 and 17 may comprise suitable gear transmission instead of belt drive.

The invention claimed is:

1. A user interface device for a surgical simulation system, comprising:
   a rigid shaft having a primary extension along a longitudinal axis, said rigid shaft being pivotably supported by a frame, and movable in relation to said frame in an axial direction, said rigid shaft being fixed in relation to said frame with respect to rotation around said longitudinal axis; and
   a handle having a sensor body rigidly attached to said rigid shaft, and a grip portion rotatable around said longitudinal axis relative said sensor body, said grip portion being adapted to transform a gripping motion of a user into a linear displacement,
   said handle further comprises:
      a rotator sleeve rotatable around said longitudinal axis relative said sensor body and said grip portion,
      a rotation sensor adapted to detect rotation of said rotator sleeve in relation to said sensor body, and
      a signal interface mounted on said sensor body and connected to receive a first detection signal from said rotation sensor.

2. The user interface device of claim 1, wherein said handle further comprises:
   a linear sensor mounted in said sensor body,
   a motion transfer arrangement for transferring any linear displacement generated in the grip portion to said linear sensor, and
   said signal interface being connected to receive a second detection signal from said linear sensor.

3. The user interface according to claim 2, wherein said motion transfer arrangement comprises a first elongated member arranged to be linearly displaced upon a gripping motion of a user, a rotatable disc and a second elongated member connected to said linear sensor,
   a first mechanical connection connecting said first elongated member to a center portion of said disc, and a second mechanical connection connecting said second elongated member to a peripheral portion of said disc,
   wherein said rotatable disc and said first and second elongated members are displaceable along said longitudinal axis, and
   wherein said first and second mechanical connections are arranged to transfer only forces acting along the longitudinal axis.

4. The user interface according to claim 2, wherein said motion transfer arrangement comprises a first elongated member arranged to be linearly displaced upon a gripping motion of a user, and a second elongated member connected to said linear sensor, a mechanical connection connecting said first elongated member and said second elongated member, wherein said first and second elongated members are displaceable along said longitudinal axis, and wherein said mechanical connection is arranged to transfer only forces acting along the longitudinal axis.

5. The user interface according to claim 4, wherein said rotation sensor has a central opening through which said second elongated member extends.

6. The user interface according to claim 1, further comprising a plurality of actuators mounted on said frame and arranged to provide force feedback to a user rotating said handle in relation to said frame around two axis.

7. The user interface according to claim 6, wherein an actuator arranged to provide force feedback around a first axis is mounted on a part of said frame that rotates with said handle around a second axis.

8. The user interface according to claim 1, wherein said rigid shaft has a rack on one side, said rack engaging a gear wheel on said frame, thereby transforming a linear motion of said shaft into a rotation of said gear wheel.

9. The user interface according to claim 8, further comprising an actuator connected to said gear wheel and arranged to provide force feedback to a user.

10. The user interface according to claim 1, further comprising means for providing force feedback to a user rotating said sleeve.

11. A surgical simulation system, comprising:
a processing unit for executing simulation software for simulating a surgical procedure,
a display for displaying a visualization of the simulated procedure, and
a user interface device according to claim 1, connected to said processing unit for allowing a user to interact with the computer simulation visualized in the display.

* * * * *